United States Patent [19]

Duivenvoorden

[11] Plant 4,982

[45] Feb. 15, 1983

[54] ROSE PLANT

[76] Inventor: Gerardus J. C. Duivenvoorden, Leidsemeerstraat 18, Buitenkaag, Netherlands

[21] Appl. No.: 224,623

[22] Filed: Jan. 12, 1981

[51] Int. Cl.[3] ..... A01H 5/00

[52] U.S. Cl. ..... Plt./25

[58] Field of Search ..... Plt./17-18, Plt./22, 25

*Primary Examiner*—Robert E. Bagwill

*Attorney, Agent, or Firm*—Synnestvedt & Lechner

[57] ABSTRACT

A new variety of rose plant of the Floribunda class, being derived as a sport of the rose "Merko", and differing therefrom in its light pink coloration, as compared to the strong orange of the original stock. Flower size ranges from 3" to 4" when full blown.

1 Drawing Figure

This invention relates to a new variety of Floribunda rose. The plant is an upright bush rose for greenhouse cultivation. Its hardiness has not yet been tested. It is a sport which was discovered by applicant in May, 1977, as a bud mutation of a MERKO rose plant growing in a greenhouse in his nursery in Buitenkaag, Holland. A bud eye of the sport was grafted by applicant on Rosa Canina Inermis understock in the course of a selective study. It can also be grafted to any conventional understock similar to R.x noisettiana manetti. The new variety is grown chiefly for industrial exploitation by professional nurserymen and for the production of cut flowers.

The new variety name or denomination is GERDO.

Its vegatative type corresponds to the parent variety MERKO (known in the United States as MERCEDES and is described in U.S. Plant Pat. No. 3,724), but, whereas the MERKO rose is strong orange in color, the new variety (GERDO) is light pink. The characteristics and properties of the new variety are strictly transmissable by agamic means — i.e., asexually. Thus, the new variety can be propagated by cuttings, grafting or budding.

Plants grown in the greenhouse produce an abundant quantity of bloom — a plant of the new variety will produce about 15 to 30 flowers per year. The flowers are usually borne singly on normal stems of medium size. The fragrance is slight or weak.

The accompanying drawing, being a photograph in color, shows, in the upper left view, the bud just after opening of the calyx, in the upper right view the new-blown flower, and in the middle view the bloom indoors, a couple of days after cutting. A compound leaf is also shown in the bottom right view, and the underside of the bloom is shown in the bottom left view. In the description that follows, color names which begin with small letters designate colors whose conventional names are sufficiently accurate to describe the color in general; color names associated with the initials RHS refer to values found in the Colour Chart of The Royal Horticultural Society, London.

BUD

The peduncle is of average length and caliper. It is erect and stiff, with very few prickles. The color of the bud as the calyx opens is RHS 33C. The bud is about 30 mm. in length, and 22 mm. in diameter. It is ovoid in form, and its light pink coloration is RHS 33C. As the first petals open, the bud is of average size and medium length. The bud opens up well, and is not retarded by environmental conditions.

BLOOM

The blooms, when they are first fully opened, are of average size, specifically, from about 75 to 100 mm. in diameter. The form of the bloom is globular, at first; the petals are tightly rolled outwardly, and later becoming more loosely rolled outwardly.

PETALS

The petals have a satiny texture on both their inner and outer surfaces. The petalage is very double — from 30 to 32 petals. The outside petals are round to broadly ovate in shape, the intermediate and inside petals being oval. In the month of August, 1979, in Aalsmeer, their general color effect was orange-red RHS 33C, when freshly opened; but red, RHS 38A, Red open for three days. The lower side margin is yellow-orange, RHS 17C.

Cut roses, greenhouse grown, last for 12 days in August.

PLANT

Foliage — The compound leaves usually have from 3 to 7 leaflets, which are oval in shape and measure about 150 mm. in length and about 93 mm. in width. The top leaflet, without petiole, is about 55 mm. in length and a maximum width of about 43 mm. The petiole is about 19 mm. in length. The mature leaf is light medium green in color on its upper surface, and medium green on its lower surface. The leaves when young are light green on the upper surfaces and light medium green on the lower.

The rachis is of average size and smooth. The stipules are moderately short.

The new variety has good resistance to disease but is mildly subject to mildew and blackspot.

It is of upright habit and is a moderate to vigorous grower. Its canes are of medium caliper. The main stems are green in color and have only a few large prickles, a few small prickles and no hairs. The large prickles are up to 5 mm. in length and 4 mm. in diameter.

The branches, under glass, are medium green. They carry no large prickles and very few small ones. There are no hairs.

The new shoots are of violet color. Like the branches, they carry no large prickles and very few small ones. There are no hairs.

I claim:

1. An asexually-reproduced rose plant of the Floribunda class, substantially as herein illustrated and described, namely, a sport of the Merko variety, and characterized particularly in the light pink coloration of its blooms, in addition to the abundance of its blooms, even though usually borne singly.

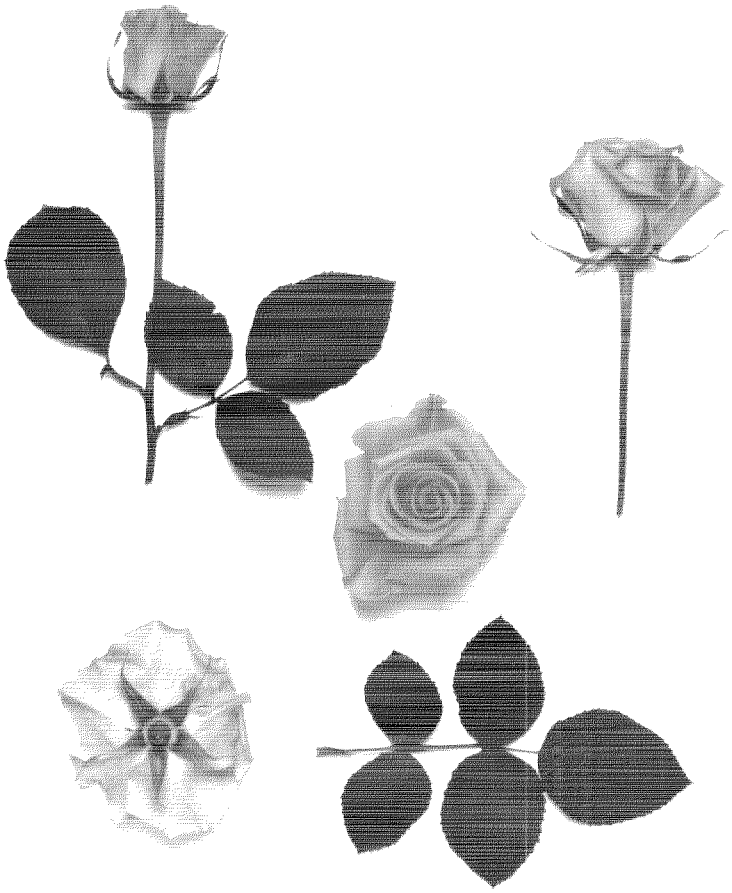

* * * * *